United States Patent [19]
Dai et al.

[11] Patent Number: 5,723,698
[45] Date of Patent: Mar. 3, 1998

[54] CATALYTIC DECOMPOSITION OF FORMATE IMPURITIES IN TERTIARY BUTYL ALCOHOL AND METHYL TERTIARY BUTYL ETHER STREAMS

[75] Inventors: Pei-Shing Eugene Dai; Laurence Darrel Neff; Kyle Lee Preston, all of Port Arthur; Rei-Yu Judy Hwan, Sugar Land, all of Tex.

[73] Assignee: Huntsman Specialty Chemicals Corporation, Austin, Tex.

[21] Appl. No.: 573,822

[22] Filed: Dec. 18, 1995

[51] Int. Cl.$^6$ .................... C07C 27/26; C07C 41/00
[52] U.S. Cl. .................... 568/913; 568/922; 568/699
[58] Field of Search .................... 502/100, 326, 502/328; 568/699, 922, 913, 920

[56] References Cited

U.S. PATENT DOCUMENTS 4,916,104  4/1990  Isogai .
5,457,243  10/1995  Knifton .

*Primary Examiner*—Gary Geist
*Assistant Examiner*—Karl J. Puttlitz, Jr.
*Attorney, Agent, or Firm*—Russell R. Stolle; Ron D. Brown; Carl G. Ries

[57] ABSTRACT

Disclosed is a method for decomposing formate esters, free acids and peroxides in a tertiary butyl alcohol stream to produce noncondensible gas products which comprises reacting said tertiary butyl alcohol stream or a methyl tertiary butyl alcohol stream containing formate esters over a catalyst comprising a non-noble Group VIII metal and a metal of Group IB on a support comprising an inert composition mixed with a hydrotalcite-like composition.

16 Claims, 5 Drawing Sheets

CATALYTIC DECOMPOSITION OF FORMATE IMPURITIES IN TERTIARY BUTYL ALCOHOL AND METHYL TERTIARY BUTYL ETHER STREAMS

FIELD OF THE INVENTION

This invention relates to purification of tertiary butyl alcohol (TBA) and methyl tertiary butyl (MTBE) streams. More particularly it relates to a catalytic process for the purification of tertiary butyl alcohol and methyl tertiary butyl ether streams from organic formate esters and free acids. Still more particularly, this invention allows a high degree of removal of formates and peroxide impurities from TBA and MTBE streams by actual decomposition rather than neutralization.

BACKGROUND OF THE INVENTION

In the operation of a plant producing propylene oxide and methyl tertiary butyl ether one of the byproducts is formic acid. This formic acid may react in downstream operations with methanol or t-butanol to form methyl formate (MeF) or t-butyl formate (TBF). The tertiary butyl alcohol feed to the MTBE reactors may contain as much as 0.4–1.3 wt % of t-butyl formate. Tertiary butyl formate can be converted to methyl formate through the trans-esterification reaction with methanol in the MTBE reactor. In the acidic medium, methyl formate is hydrolyzed to form formic acid and methanol. Formic acid causes severe corrosion problems in the carbon steel vessels. Methyl formate is irreversibly converted to formate salt in a basic medium.

One method of addressing this problem is to neutralize methyl formate by the injection of a strong base such as, for example, KOH or NaOH. The problem with this method is that the potassium or sodium formate, thus formed, is disposed into a waste water stream and the residual caustic in the waste water stream can catalyze a number of undesirable side-reactions to generate C7–C11 ketones from acetone. In addition, the cost of injecting these caustics can be in the multiple millions of dollars.

Peroxide contaminants have been removed from motor-fuel grade tertiary butyl using catalysts. In U.S. Pat. No. 4,705,903, motor-fuel grade tertiary butyl alcohol which is prepared by reacting propylene with tertiary butyl hydroperoxide to form propylene oxide and a tertiary butyl alcohol (tBuOH) reaction product contaminated with residual amounts of tertiary butyl hydroperoxide and di-tertiary butyl peroxide was effectively treated under mild conversion conditions with a catalyst composed of iron, copper, chromia and cobalt in order to convert the two peroxide contaminants to tBuOH.

In U.S. Pat. No. 4,742,179 contaminated motor fuel grade tertiary butyl alcohol is treated with a base-treated hydrogenation catalyst from Groups VIB or VIIIB in order to selectively convert the two peroxide contaminates to tertiary butyl alcohol.

In U.S. Pat. No. 4,873,380, contaminated motor fuel grade tertiary butyl alcohol is treated with a catalyst consisting essentially of nickel, copper, chromium, and barium to substantially selectively convert the two peroxide contaminants to tertiary butyl alcohol.

In U.S. Pat. No. 5,457,243 there is disclosed a method for neutralizing organic acids in a crude methyl tertiary butyl ether stream over solid bases. Disadvantages are that the adsorption capacity of solid bases is generally low and therefor requires an excessively large bed or frequent regeneration of solid bases.

Methyl formate can be decomposed to give methanol and high purity CO by decarbonylation which is represented by $HCOOCH_3 \rightarrow CH_3OH+CO$. In the catalytic decarbonylation of methyl formate, $CH_3OH$ and CO are desired products and methane and dimethylether are the main by-products. A number of methods are available for decarbonylation of methyl formate. Heterogeneous catalysts such as $Al_2O_3$, SrO, BaO, ZnO, zeolite and MgO were reported to be effective. KCl and KOH supported on activated carbon were at one time considered for commercial application by Mitsubishi Gas Chemicals in Japan (T. Ikarashi, Chem Econ. Eng. Rev. 12 (1980) 31, nickel catalysts are also known to catalyze the decarbonylation.

Other researchers have investigated the catalytic decarboxylation of methyl formate over an alkaline metal salt supported on various supports. Active carbon and active carbon supported potassium carbonate showed the highest conversion levels of methyl formate (85.2–88.9%) at 300° C. The selectivity to $CH_3OH$ was about 86.6%, and to dimethyl ether about 11.2–4.3%. Magnesia-based catalysts were less active, but showed better selectivity toward $CH_3OH$ with negligible side reactions such as decarboxylation and ether formation.

Hydrogenolysis of methyl formate in the presence of hydrogen gives methanol: $HCOOCH_3+2H_2 \rightarrow CH_3OH$. This reaction has been extensively studied in both the liquid-phase and/or gas phase. Copper chromite catalysts such as United Catalysts G-89 and Engelhard 1808 are known to provide a good system for the hydrogenolysis of methyl formate. Near equilibrium conversion values (for example <60%) can be obtained at moderate conditions (130°–195° C. and 1 atm). It is noteworthy that decomposition of formic acid to hydrogen and carbon dioxide catalyzed by supported metal catalysts can be achieved with 50% conversion at the same temperature range.

It would represent a distinct advance in the art if there were a method available for removing methyl formate and peroxide impurities from tertiary butanol and MTBE streams in a manner such that these chemicals would not be just neutralized, but would be completely broken down to noncondensible gas products, such as hydrogen, carbon monoxide, carbon dioxide, and methane as well as liquid products such as TBA, MeOH, and isobutylene.

A high degree of removal of formate would reduce consumption of caustic, reduce the potential for corrosion problems caused by formates, alleviate the problem of having high total organic content in the waste water stream and thereby permit a PO/MTBE plant to run at full design capacity.

SUMMARY OF THE INVENTION

In accordance with the foregoing this invention is directed to a method for decomposing the formate esters in tertiary butyl alcohol and methyl tertiary butyl alcohol streams to produce noncondensible gas products which comprises reacting a tertiary butyl alcohol stream or a methyl tertiary butyl alcohol stream containing formate esters over a catalyst comprising an alkali metal, a non-noble Group VIII metal and a metal of Group IB on a support comprising an inert composition mixed with a hydrotalcite-like composition.

DESCRIPTION OF THE INVENTION

Figure 1:
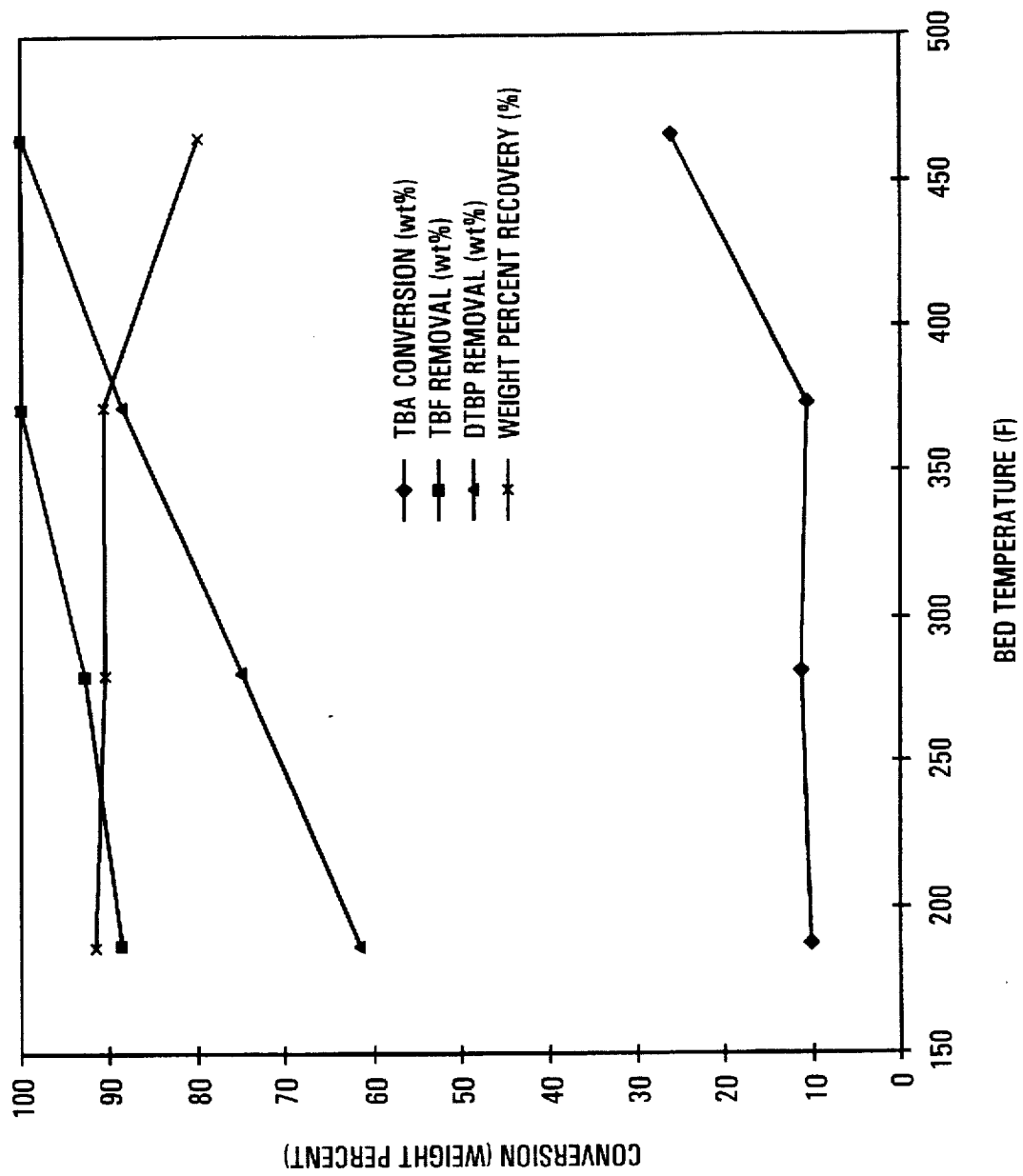
FIG. 1 Decomposition of organic formates over 50% DHT-4A/alumina catalyst.

This invention provides a process for purification of TBA and MTBE streams. The formate esters (TBF and MEF) and formic acid as well as peroxides (di-tertiary butyl peroxide [DTBP]) and allyl butylperoxide (ATBP) can be removed by contacting the TBA feed with a hydrotalcite composition/alumina based catalyst containing Group IB and VIII metals. The reactor suitable for this process may be fixed-bed, ebullated-bed or catalytic distillation reactor. The desired process temperature and pressure are 250°–500° F. and 100–600 psi. The total metal content may be in the range of 0–40 wt % of the finished catalyst. The concentration of hydrotalcite composition in the support may range for 5–100%.

The charge stream which may be treated in the instant invention in order to decompose formate esters is a tertiary butyl alcohol or methyl tertiary butyl ether stream. An example is the tertiary butyl alcohol stream obtained from a t-butyl alcohol Day Tank from a PO/MTBE plant which would typically contain about 0.2–1.2 wt % tertiary butyl formate and about 0.1–1.0 wt % organic peroxides.

The catalyst comprises metals of Group IB and VIII on a support.

The catalyst is formed on a support which contains 2–75 parts, preferably 25–75 parts, say 50 parts of inert composition—typically metal oxide-type support such as alumina, silica, silica-alumina, magnesia, titania, etc. The preferred support is alumina, preferably gamma alumina.

There is mixed with the support, a hydrotalcite-like composition of the formula:

$[X_a Y_b (OH)_c]_n [A]_d \cdot e H_2O$ a=1–10
b=1–10
c=2 (a+b)=4–40
A is an anion of formal negative charge n
n=an integer 1–4
d is the formal positive charge of $[X_a Y_b (OH)_c]$
e=1–10
X is a divalent metal
Y is a trivalent metal of Group III or Group VI-B or non-noble Group VIII of the Periodic Table,
subject to the qualification that when one of d or n is an integral multiple of the other, they are both reduced to lowest integral terms. This is discussed in U.S. Pat. No. 5,340,466 and U.S. Pat. No. 5,459,118, incorporated herein by reference in its entirety.

The metal X may be a Group II-A metal such as beryllium (Be), magnesium (Mg), calcium (Ca), strontium (Sr), barium (Ba), or radium (Ra). The preferred metal is magnesium (Mg). More than one metal X may be present.

The metal Y may be boron (B), aluminum (Al), gallium (Ga), indium (In), or thallium (Tl) of Group III, or iron Fe, cobalt Co, or nickel Ni of non-noble Group VIII, or chromium Cr, molybdenum, Mo, or tungsten W of Group VI-B. The preferred metal is aluminum (Al). More than one metal Y may be present.

a may be 1–10, preferably 3–6, say 4.5.
b may be 1–10, preferably 1–3, say 2.
c may be 4–40, preferably 10–16, say 13.
n may be an integer 1–4, preferably 1–2, say 2.
d may be 1–4, preferably 1.
e may be 1–10, preferably 3–4, say 3.5

A may be an anion such as $CO_3^=$, halogen eg. Cl—, acetate $C_2H_3O_2$—, oxalate $HC_2O_4^-$ or $C_2O_4^=$, $NO_3^-$, $SO_4^=$, or $ClO_4^-$. The preferred anion may be $CO_3^=$.

Illustrative hydrotalcite-like (HTlc) compositions may be those noted in the following table—the first listed (hydrotalcite (HT) itself), available under the designation DHT-4A is preferred:

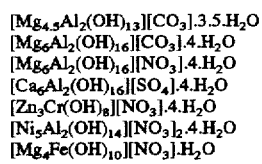

Hydrotalcite $[Mg_6Al_2(OH)_{16}CO_3 \cdot 4H_2O]$ is a hydroxycarbonate of magnesium and aluminum and occurs naturally in the Urals of the Soviet Union and also in Snarum, Norway. In 1966 Kyowa Chemical Industry Co., Ltd. succeeded in the world's first industrial synthesis of hydrotalcite. (U.S. Pat. Nos. 3,539,306 and 3,650,704). DHT-4A $[Mg_{4.5} Al_2(OH)_{13}CO_3 \cdot 3.5H_2O]$ is a hydrotalcite-like compound. The first papers in the literature referring to hydrotalcite-like compounds appeared in 1971, written by Miyata et al., dealing with basic catalysts (S. Miyata et al., Nippon Kagaku Zasshi, 92 (1971) 514) and in 1977 by Miyata (S. Miyata, Kogaku Gijutsushi Mol, 15 (10) (1977) 32 and 15 (3) 1971 31).

The preparation, properties and applications of hydrotalcite-type anionic clays are reviewed by F. Cavani et al in CATALYSIS TODAY, Vol. 11, No. 2, 1991. The properties of the DHT-4A product are detailed in the data sheets provided by Kyowa Chemical. The natural product of calcination or activation in inert gas of a HTlc is believed to be a spinel. In the range between the temperature at which HTlc decomposition commences (between 572° and 752° F.) and that of spinel formation (1652° F.), a series of metastable phases form, both crystalline and amorphous. Therefore, the surface area, pore volume, and structure depend on the temperature of calcination. Upon calcination, the crystal structure of DHT-4A is decomposed at about 660° F. when water and carbon dioxide evolved from the structure, and a MgO—$Al_2O_3$ solid solution of formula 4.5 MgO.$Al_2O_3$ is formed. This solid solution is stable up to 1472° F. MgO and $MgAl_2O_4$ are formed at about 1652° F. On the other hand, the solid solution calcined at less than 1472° F. can be restored to the original structure by hydration.

The most interesting properties of the calcined hydrotalcite are 1) high surface area, 2) basic properties, and 3) formation of homogeneous mixtures of oxides with very small crystal size. Miyata et al., showed that there is a maximum in the number of basic sites when the hydrotalcite is calcined at 932° F. Nakatsuka et al. examined the effect of the Mg/Al ratio in the hydrotalcite on the basic strength and the amount of basic sites. (Bull. Chem. Soc. Japan, 52 (1979) 2449). The number of basic sites increased with Mg/Al ratio, while the number of acid sites decreased; however the compound with ratio MgO/$Al_2O_3$ of 5.23 exhibited the greatest number of basic sites per unit of surface area. The hydrotalcite and the calcined hydrotalcite have found applications in basic catalysis, hydrogenation of nitrobenzene, oxidation reaction, and support for Ziegler-Natta catalysts. U.S. Pat. No. 4,962,237 discloses a catalytic process for the preparation of polyols using the calcined DHT-4A.

The compositions are available commercially from Kyowa Chemical Industry Co. Ltd. of Kagawa, Japan. The preferred composition is marketed under the trademark DHT-4A having the formula:

$$Mg_{4.5}Al_2(OH)_{13}CO_3 \cdot 3.5H_2O.$$

The catalyst support may be formed by mixing 10–840 parts, preferably 200–750 parts, say 300 parts of hydrotalcite-like composition with 360–1190 parts, preferably 500–1000 parts, say 900 parts of inert support, preferably 700–900 parts, say 800 parts of water and 5–40 parts, preferably 10–30 parts, say 24 parts of acid such as nitric acid. After mulling, the mixture is cast or extruded to form cylinders of diameter of about 0.8–1.6 mm, say 1.3 mm and length of 2.5–15 mm, say 3.8 mm. The cross-section of the particles is preferably a trilobar.

The particles are dried at 220° F.–400° F., preferably 220° F.–300° F., say 220° F. for 10–30, preferably 12–24, say 16 hours and thereafter calcined at 1000° F.–1200° F., preferably 1050° F.–1150° F., say 1100° F. for 0.2–3 hours, preferably 0.4–2 hours, say 0.5 hours.

The so-formed composition is typically characterized by the following properties:

TABLE

| Property | Broad | Preferred | Typical |
|---|---|---|---|
| Total Pore Vol. cc/g | 0.5–1 | 0.7–0.9 | 0.7 |
| Pore Size Dist. cc/g | | | |
| >1500A | 0.001–0.02 | 0.01–0.02 | 0.011 |
| >500A | 0.01–0.5 | 0.01–0.4 | 0.014 |
| >250A | 0.01–0.5 | 0.01–0.02 | 0.014 |
| >100A | 0.15–0.6 | 0.2–0.6 | 0.22 |
| <100A | 0.3–0.6 | 0.35–0.55 | 0.50 |
| Pore Mode A | | | |
| dv/dD Max | 55–65 | 57–63 | 61 |
| BET | 55–65 | 60–65 | 63 |
| Total Surface Area | | | |
| m²/g | 200–350 | 220–335 | 330 |

Preparation of the catalyst of this invention is effected by contacting the support with preferably aqueous solutions of Group I-B and non-noble Group VIII metal. The non-noble Group VIII metal may be iron (Fe), cobalt (Co), or nickel (Ni), preferably cobalt; and the metal may be added, in solution in an amount sufficient to fill the pores of the support—preferably as an aqueous solution of a soluble nickel salt such as the acetate, nitrate, carbonate, etc. The Group I-B metal may be copper, silver or gold, preferably copper employed in an aqueous solution.

The metals may be added simultaneously or sequentially. After addition, the support bearing the metals is dried at 50° F.–100° F., preferably 60° F.–90° F., say 70° F. for 0.5–24 hours, preferably 1–4 hours, say 2 hours, and then at a higher temperature of 220° F.–400° F., preferably 250° F.–300° F., say 250° F. for 1–8 hours, preferably 2–6 hours, say 4 hours. Thereafter the catalyst is calcined at 600° F.–1000° F., preferably 700° F.–900° F., say 800° F. for 1–8 hours, preferably 2–6 hours, say 4 hours, and thereafter at higher temperature of 800° F.–1200° F., preferably 900° F.–1100° F., say 1010° F. for 0.5–5 hours, preferably 1–3 hours, say 2 hours.

The finished catalyst may be characterized as follows (parts by weight):

TABLE

| Property | Broad | Preferred | Typical |
|---|---|---|---|
| Inert Support | 2–75 | 25–75 | 50 |
| Hydrotalcite-like Composition | 25–98 | 25–75 | 50 |
| Group VIII | 0.1–5 | 0.5–3 | 1 |
| Group I-B | 1–30 | 5–25 | 12 |

A preferred catalyst includes:

(i) 25–98 wt %, say 43.5 wt %, of the DHT-4A (from Kyowa Chemical) synthetic hydrotalcite-like composition containing:
$Mg_{4.5}Al_2(OH)_{13}CO_3 \cdot 3.5H_2O$
(ii) 2–75 wt %, say 43.5 wt %, of gamma alumina
(iii) 0.1–6 wt %, say 1 wt %, of Ni
(iv) 1–30 wt %, say 12 wt %, of Cu The percentage figures for Cu, and Ni are % of metal in the finished catalyst wherein the metal is present either in the form of oxide or in the metallic state.

The process of catalytic removal of formates and peroxides was conducted using a fixed-bed downflow reactor made of ⅝" OD×17" long stainless steel tubing. 11 cc of catalyst granules having 20–30 mesh sizes was loaded into the center zone of catalyst bed in the reactor. The feedstock used in the catalyst screening is the tertiary butyl alcohol (TBA) obtained from TBA Day Tank of the PO/MTBE plant, which contains typically about 0.2–1.2 wt % tertiary butyl formate (TBF) and about 0.1–1.0 wt % organic peroxides.

The catalyst granules were dried at 200°–600° F. for 2 hours in a stream of nitrogen gas at a rate of 50 cc/min prior to contacting with the feed. The liquid feed rate was varied from 11 to 33 cc/hr (LHSV=1–3). The feed was pumped under 300 psi back pressure. The TBA feed and nitrogen were mixed and preheated at 120°–180° F. before entering the reactor. The reactor temperature was either maintained at constant level while LHSV was varied or raised from 200° to 500° F. when LHSV was fixed at one. The typical test conditions are: nitrogen feed rate 50 cc/hr; TBA feed rate 11 cc/min (LHSV=1; 300° F.; and 300 psi). During the 48-hour test period samples of reactor effluent were withdrawn and the compositions were analyzed by gas chromatography.

Practice of the method of this invention will be apparent to those skilled in the art from the following examples. The examples are only for illustration and the invention is not intended to be limited thereby.

EXAMPLE 1

The catalyst support is prepared by mixing:
(i) Three pounds of DHT-4A powder (from the Kyowa Chemical Industry Co. Ltd. of Kagawa, Japan) having the formula:

$Mg_{4.5}Al_2(OH)_{13}CO_3 \cdot 3.5H_2O$ and (ii) Nine pounds of alpha alumina monohydrate containing 2 wt % silica as a binder. The moisture content is adjusted by adding 8 pounds of deionized water and 108 ml of 70 wt % nitric acid.

The mixture is mulled to homogeneity and extruded into trilobe cylindrical pellets of maximum width of 1.3 mm and length of about 3.8 mm. The wet pellets are dried at 220° F. for about 16 hours and calcined at 1100° F. for 0.5 hours.

The Total Surface Area (TSA) of this support is 330 m²/g and the Total Pore Volume (TPV) by mercury porosimetry is 0.72 cc/g. This support contains 16 wt % MgO and 84 wt % $Al_2O_3$/

Prior to impregnation, the support is dried again at 250° F. overnight (18 hours). The impregnation solution is prepared by dissolving 18 parts of copper nitrate and 2 parts of nickel nitrate hexahydrate in 80 parts of deionized water at 140° F.

The ratio of total volume of impregnating solution to Total Pore Volume (as measured by mercury porosimetry) is about 1.0–1.5:1. The support (30 g) is impregnated with 35 ml of solution. The wet support is permitted to stand at room temperature for 0.5 hours, dried at 250° F. for 2 hours, calcined at 800° F. for 3 hours, and finally calcined at 1000° F. for 1 hours.

The composition and properties of the supports and the finished catalysts are set forth in the Tables infra.

EXAMPLE 2

Preparation of DHT-4A/Alumina with 6% Cu, 0.5% Ni

Support: 50% DHT-4A/Alumina 1. 59.00 grams of copper nitrate, Cu $(NO_3)_2.2.5H_2O$ and 6.50 grams of nickel nitrate, Ni $(NO_3)_2.6H_2O$, were dissolved in distilled water—The total volume was 335 ml.

2. 251 grams of support was impregnated at room temperature dried at 250° F. for two hours and calcined at 800° F./3-Hrs., 1000° F./1-Hr.

EXAMPLE 3

Support: 25% DHT-4A/Alumina 1. 33.80 grams of copper nitrate, $Cu(NO_3)_2.2.5H_2O$ and 3.75 grams of nickel nitrate, $Ni(NO_3)_2.6H_2O$, were dissolved in distilled water—The total volume was 165 ml.

2. 144.16 grams of support was impregnated at room temperature, dried at 250° F. for two hours and calcined at 800° F./3-Hrs., 1000° F./1-Hr.

EXAMPLE 4

Preparation of DHT-4A/Alumina with 12% Cu, 1% Ni

Support: 50% DHT-4A/Alumina, SN-7255

1. 15.15 grams of copper nitrate, $Cu(NO_3)_2.2.5H_2O$ and 1.71 grams of nickel nitrate, Ni $(NO_3)_2.6H_2O$, were dissolved in distilled water—Total Volume 40 ml.

2. Thirty (30) grams of support was impregnated at room temperature, dried at 250° F. for two hours and calcined at 800° F./3-Hrs., 1000° F./1-Hr.

EXAMPLE 5

Support: 25% DHT-4A/Alumina, SN-7097A 1. 15.15 grams of copper nitrate $Cu(NO_3)_2.2.5H_2O$ and 1.71 grams of nickel nitrate, Ni $(NO_3)_2.6H_2O$, were dissolved in distilled water—The total volume was 35 ml.

2. Thirty (30) grams of support was impregnated at room temperature, dried at 250° F. for two hours and calcined at 800° F./3-Hrs., 1000° F./1-Hr.

RESULTS

The data summary of formate decomposition over 50% DHT-4A/Alumina at various temperatures is presented in Table I. The TBA feed contains at least three kinds of formate esters, namely, 0.63% tertiary butyl formate (TBF) and 0.031% isopropyl formate (IPF) and 0.32% isobutyl formate (IBF). The feed also contains 0.53% di-tertiary butyl peroxide (DTBP) and 0.36% secondary butyl acetate (SBA). The conversions for all five components are shown in Table I. It is seen that TBF removal greater than 90% can be attained at temperature higher than 282° F. Complete removal of di-tertiary butyl peroxide can be achieved at temperature higher than 421° F. Over the temperature range of 200°–500° F., the TBA dehydration is below 30%.

Table II gives the data summary of formate decomposition over 6% Cu and 0.5% Ni on 50% DHT-4A/Alumina at various temperatures. TBF removal greater than 90% can be obtained at temperature as low as 188° F. The catalyst also showed very significant improvement in the DTBP decomposition at lower reactor temperatures compared to the support. This CuNi catalyst exhibited a TBA conversion lower than 20% in the entire temperature range.

In Table III, the catalysts of this invention, Examples I–IV, are compared with the control examples, Examples V–IX for their TBF, DTBP and TBA conversions. The results clearly show that the catalysts of this invention are superior to the control catalysts in TBF and DTBP conversions. The catalytic performance of Example IV catalyst is presented in Table IV. It is seen that the catalyst gave very high activities (>90%) for TBF and DTBP removal at LHSV=1, and 2.

FIG. 1 shows the effect of reaction temperature on TBF and TDBP removal, TBA conversion, and weight percent recovery for 50% DHT-4A/Alumina catalyst (Example I). The decomposition of TBF and DTBP leads to the formation of noncondensible gas products including CO, $CO_2$, $H_2$, and $CH_4$. The dehydration of TBA gives a gas product, isobutylene, and a liquid product, water. When the reaction temperature is increased, the conversions of TBA, TBF and DTBP are increased, and therefore the amount of gaseous products is increased. The weight percent recovery of total liquid product decreases with increasing temperature.

Figure 2:
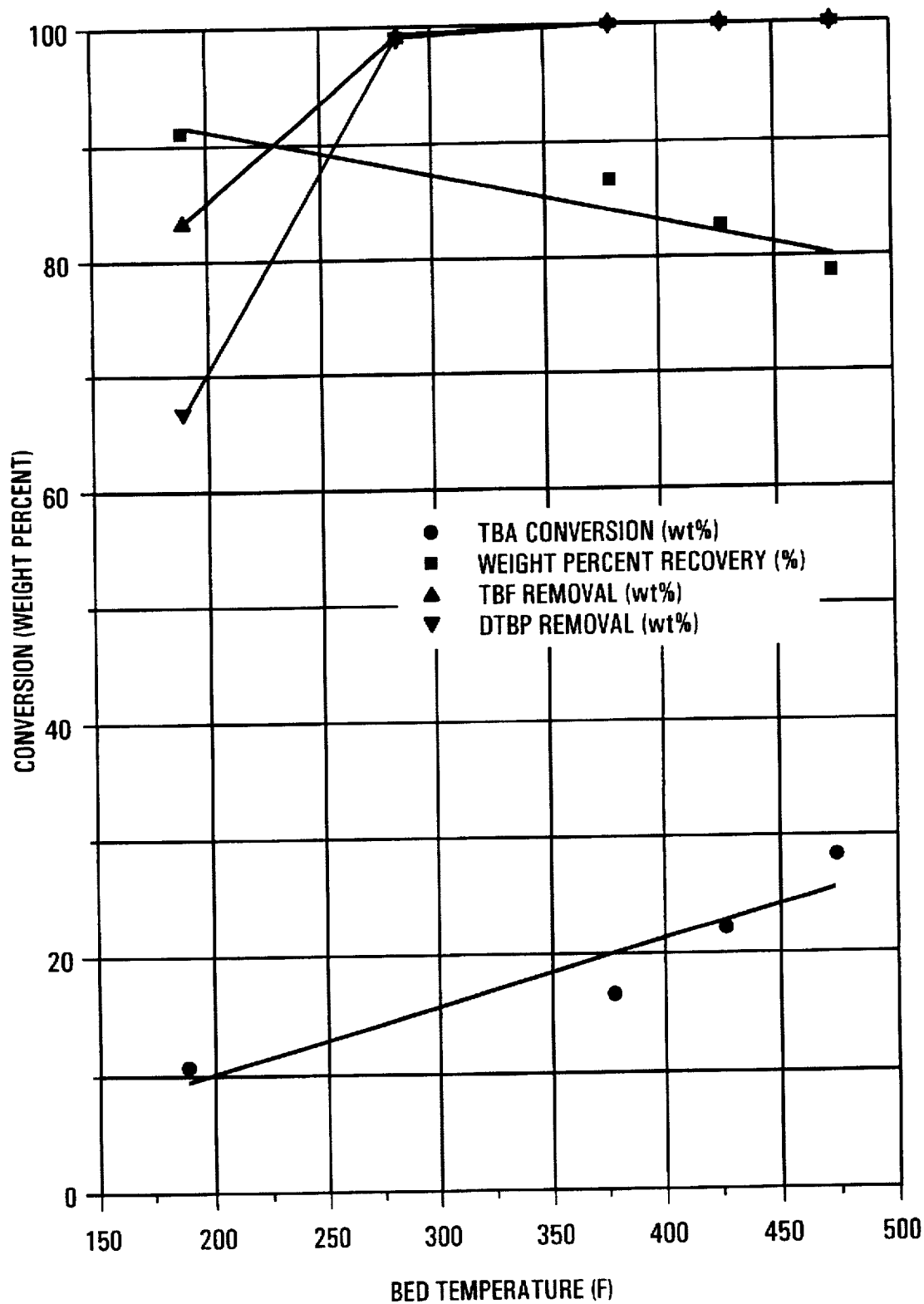
FIG. 2 Decomposition of organic formates over 6% Cu, 0.5% Ni catalyst on 25% DHT-4A/alumina support.
Figure 3:
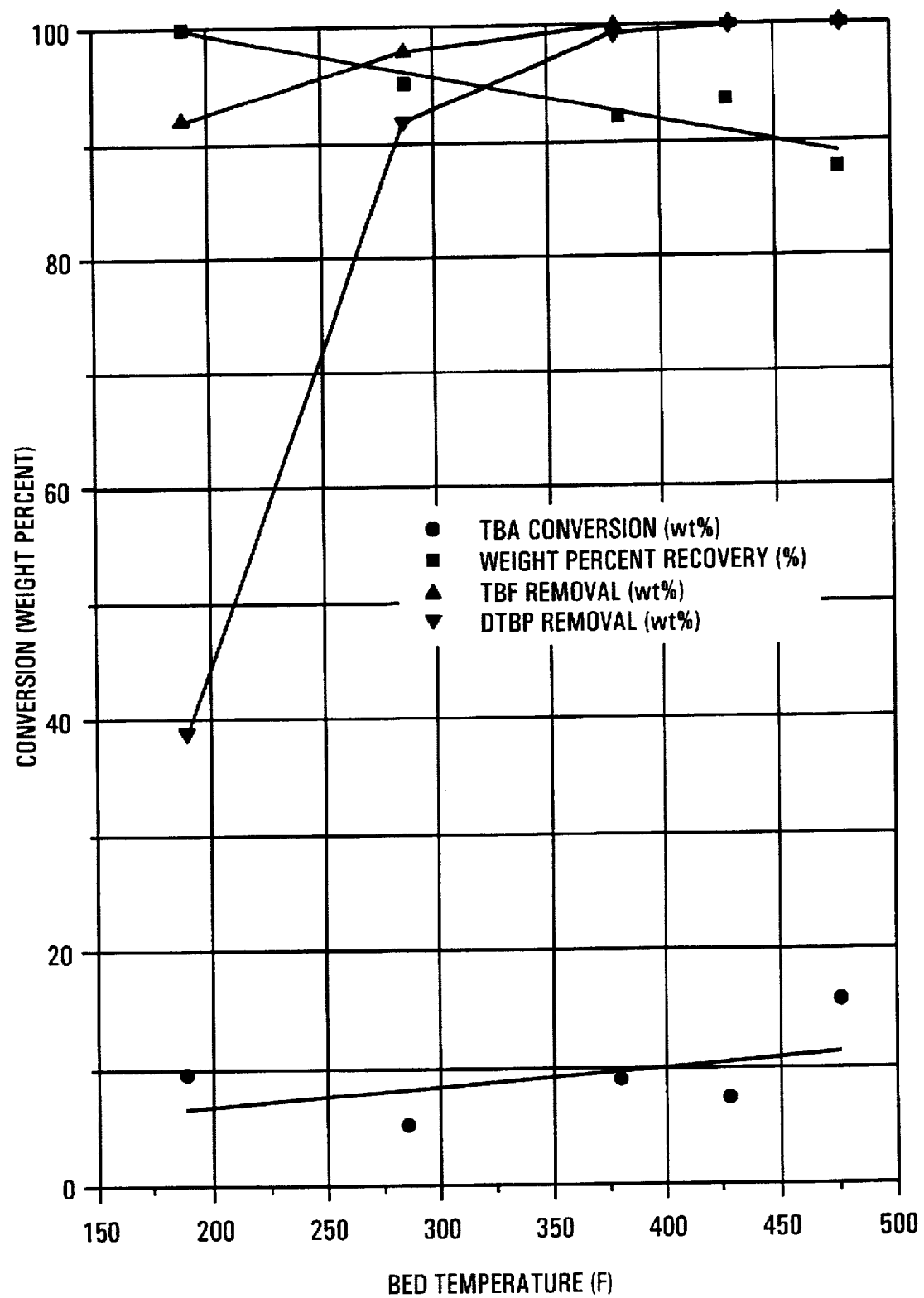
FIG. 3 Decomposition of organic formates over 6% Cu, 0.5% Ni catalyst on 50% DHT-4A/alumina support.

FIGS. 2 and 3 show similar plots for 6% Cu, 0.5% Ni on both 25% and 50% DHT-4A/Alumina, (Examples III and IV) respectively. It is noted that an increased percentage of DHT-4A, because of its basic nature, is less active for dehydration than alumina. Another advantage of DHT-4A is that the amount of undesired ether products such as dimethyl ether (DME), diisopropyl ether (DIPE) formed by dehydration reactions is also less than that for alumina.

Figure 4:
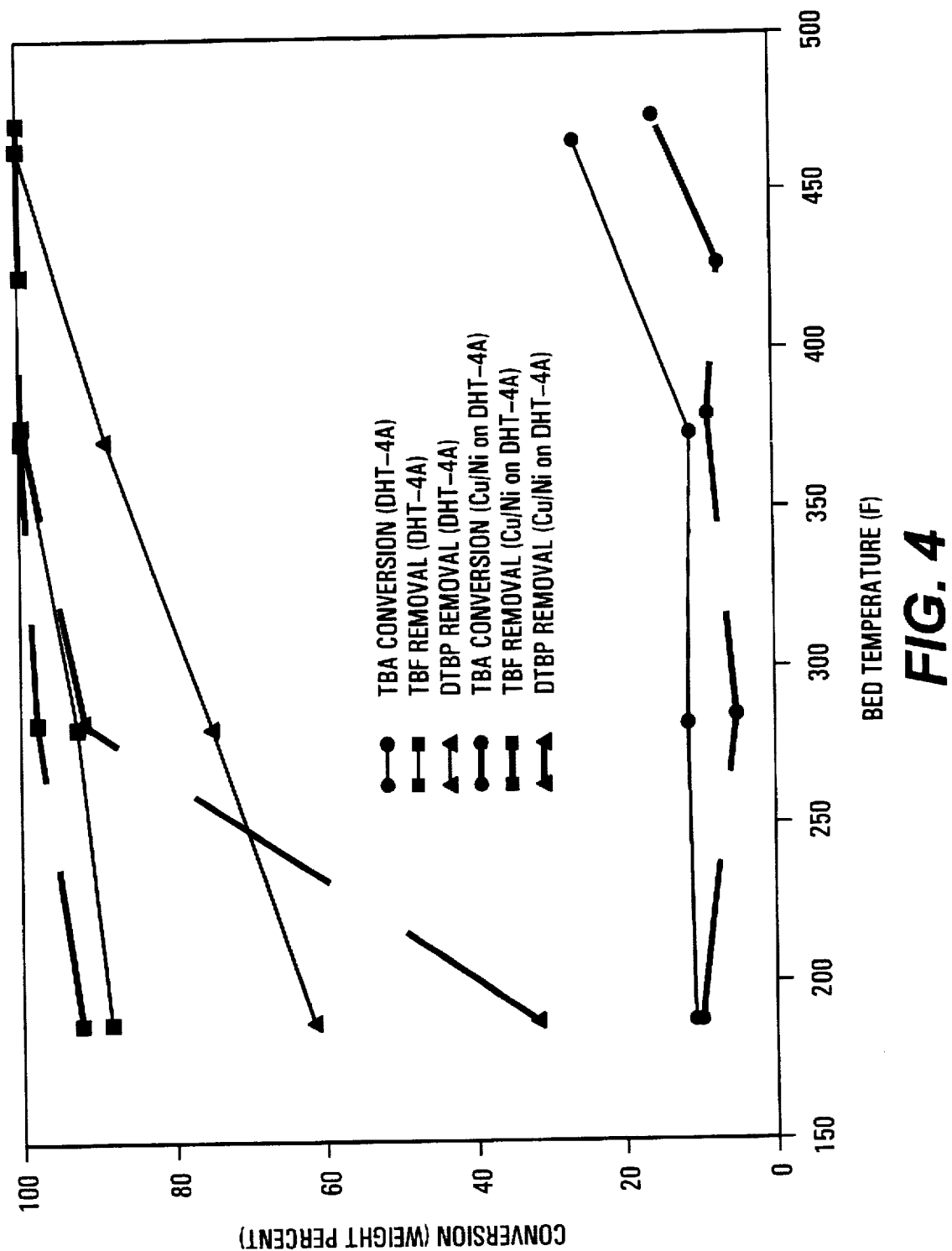
FIG. 4 Comparison of catalyst performance between CuNi catalyst and 50% DHT-4A/alumina support.
Figure 5B:
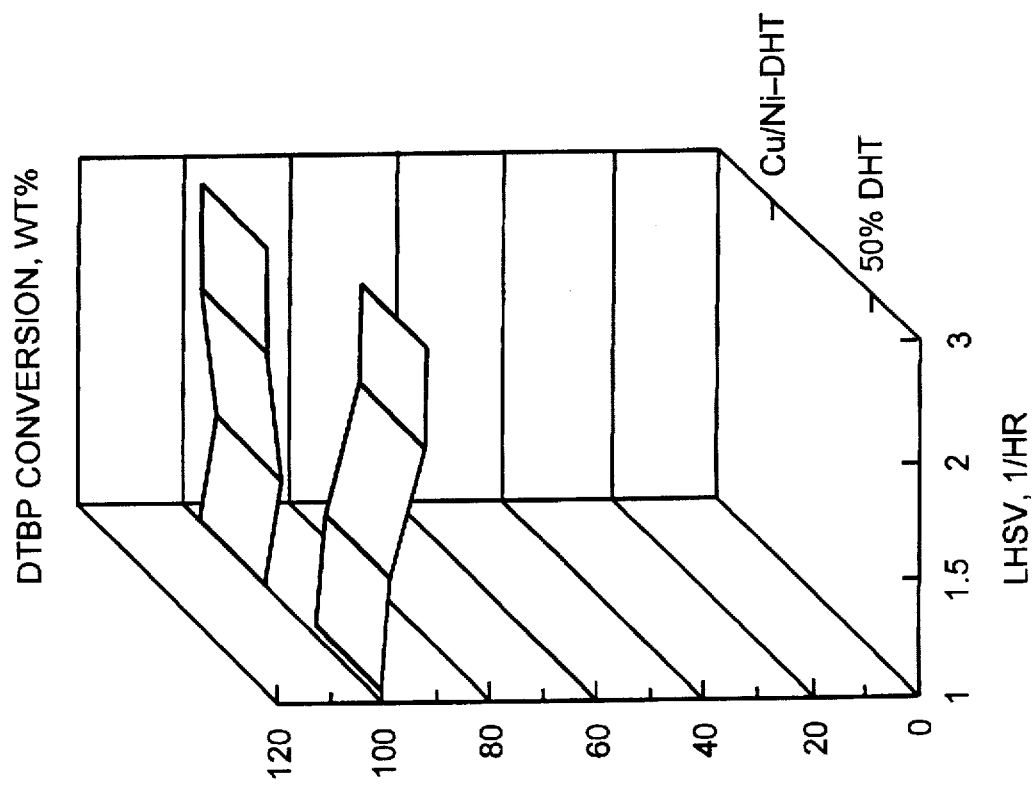
FIG. 5 Effect of tBA feed rate on formate and peroxide decomposition.
Figure 5A:
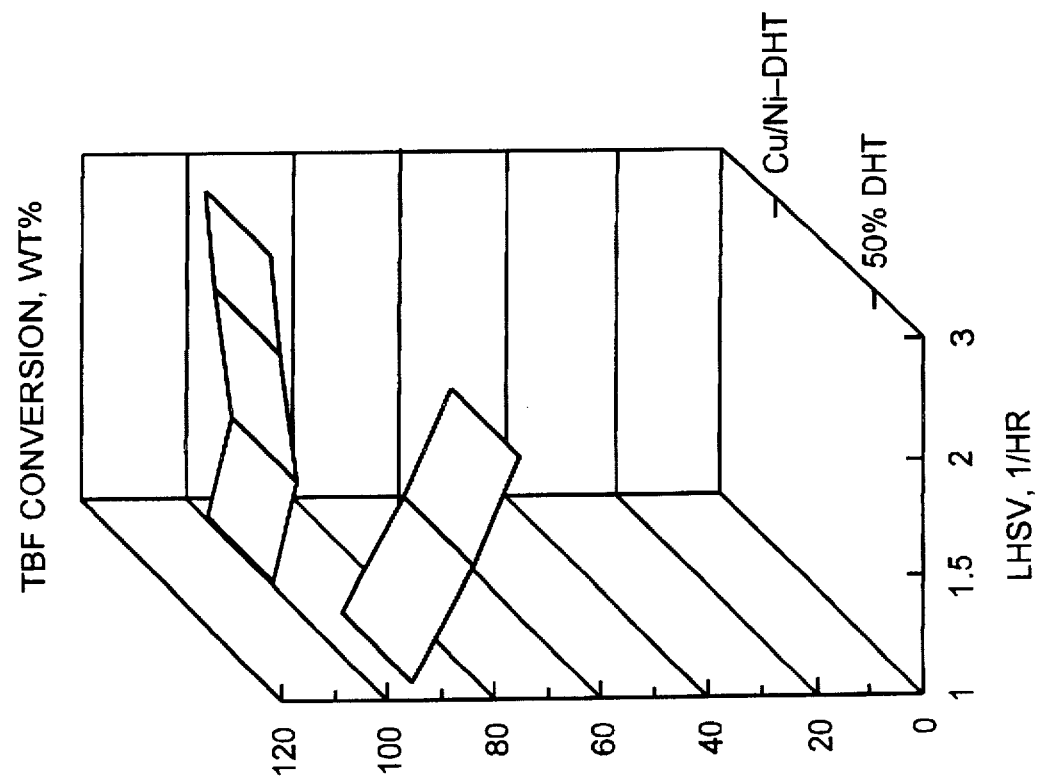

In FIG. 4, Examples IV and I are compared for their relative performances to illustrate the advantage of metals in the catalyst. The incorporation of metals, Cu and Ni, significantly improves the activity for DTBE decomposition in the preferred range of process temperature of 250°–400° F. The effect of TBA feed rate (or liquid hourly space velocity) on TBF and DTBP conversions is shown in FIG. 5 for Examples IV and I. It appears that t-butyl formate conversion over CuNi/DHT-4A (Example IV) is almost independent of LHSV, whereas, over 50% DHT-4A (Example I) TBF conversion declines with increased LHSV. For di-tertiary butyl peroxide decomposition, there is no significant difference between the two catalysts in their dependency on LHSV.

TABLE I

Data Summary of Formate Decomposition Over 50% DHT-4A/Alumina at Various Temperatures

| Bed Temperature (°F.) | Weight Percent Recovery (%) | TBA Conversion (Wt %) | IPF Removal (Wt %) | TBF Removal (Wt %) | IBF Removal (Wt %) | DTBP Removal (Wt %) | SBA Removal (Wt %) |
|---|---|---|---|---|---|---|---|
| 188 | 91.5 | 10.3 | 37.6 | 88.4 | 97.0 | 61.6 | 50.5 |
| 282 | 90.4 | 11.5 | 63.4 | 82.7 | 100.0 | 54.8 | 63.9 |
| 373.5 | 90.7 | 10.7 | 100.0 | 100.0 | 100.0 | 88.7 | 100.0 |
| 466.5 | 80.0 | 26.2 | 26.4 | 100.0 | 100.0 | 100.0 | 100.0 |
| 421 | 100.3 | 0.0 | 67.8 | 100.0 | 100.0 | 100.0 | 100.0 |

TABLE II

Data Summary of Formate Decomposition Over 6% Cu and 0.5% Ni on 50% DHT-4A/Alumina at Various Temperatures

| Bed Temperature (°F.) | Weight Percent Recovery (%) | TBA Conversion (Wt %) | IPF Removal (Wt %) | TBF Removal (Wt %) | IBF Removal (Wt %) | DTBP Removal (Wt %) | SBA Removal (Wt %) |
|---|---|---|---|---|---|---|---|
| 188 | 105.5 | 0.0 | 0.0 | 92.2 | 100.0 | 31.8 | 100.0 |
| 235 | 94.9 | 4.8 | 0.0 | 97.8 | 100.0 | 92.0 | 100.0 |
| 379 | 91.9 | 8.7 | 100.0 | 100.0 | 100.0 | 100.0 | 100.0 |
| 427 | 93.4 | 6.9 | 100.0 | 100.0 | 100.0 | 100.0 | 100.0 |
| 475 | 87.5 | 15.4 | 100.0 | 100.0 | 100.0 | 100.0 | 100.0 |

TABLE III

RESULTS OF CATALYST EVALUATION FOR DECOMPOSITION OF TBF AND DTBP IN TBA FEED SCREENING OF CATALYST SUPPORTS

| CATALYST | TEMP. °F. | TBF | DTBP | TBA |
|---|---|---|---|---|
| 50% DHT-4A/Alumina | 374 | 100 | 89 | 12 |
| Example I | 282 | 93 | 55 | 13 |
|  | 188 | 88 | 62 | 11 |
| 25% DHT-4A/Alumina | 370 | 96 | 100 | 13 |
| EXAMPLE II | 282 | 96 | 99 | 7 |
|  | 189 | 92 | 27 | 10 |
| CuNi/25% DHT-4A Alumina | 378 | 100 | 100 | 16 |
|  | 284 | 99 | 99 | 14 |
| EXAMPLE III | 189 | 83 | 67 | 11 |
| CuNi/50% DHT-4A Alumina | 379 | 100 | 100 | 9 |
|  | 285 | 98 | 92 | 5 |
| EXAMPLE IV | 188 | 92 | 32 | 10 |
| UCI MgO | 377 | 23 | 68 | 5 |
| Example V | 283 | 18 | 25 | 5 |
|  | 188 | 26 | 28 | 11 |
| Calsicat MgO | 377 | 90 | 83 | 11 |
| EXAMPLE VI | 284 | 40 | 54 | 8 |
|  | 188 | 100 | 26 | 7 |
| Norton ZrO₂ | 374 | 69 | 93 | 8 |
| EXAMPLE VII | 285 | 55 | 50 | 15 |
|  | 188 | 100 | 38 | 13 |
| TK-753 γ/Al₂O₃ | 379 | 65 | 92 | 14 |
| EXAMPLE VIII | 283 | 51 | 31 | 6 |
|  | 188 | 59 | 13 | 8 |
| HTC-400 θ/Al₂O₃ | 374 | 67 | 98 | 4 |
| EXAMPLE IX | 277 | 47 | 30 | 4 |
|  | 189 | 52 | 23 | 5 |

Reaction Conditions: TBA Day-Tank Feed, LHSV 1.0, 300 psi

TABLE IV

SUMMARY FOR TBA DEHYDRATION AND CONTAMINANTS DECOMPOSITION OVER 12% Cu, 1% Ni ON SN-7255, 50% DHT-4A ALUMINA

Catalyst ID: 052-95-6949-020, 12% Cu., 1% Ni on SN-7255, 50% DHT-4A Alumina
Run No: 095-95-0056-0000

| Bed Temperature (F) | TBA Conversion (Wt. %) | TBF Removal (Wt. %) | DTBP Removal (Wt. %) | Weight Percent Recovery (%) | LHSV |
|---|---|---|---|---|---|
| 365 | 2.0 | 99.0 | 98.2 | 96.0 | 1 |
| 368 | 0 | 93.7 | 94.6 | 93.2 | 2 |
| 368 | 8.6 | 59.1 | 84.9 | 72.7 | 3 |

The data in Tables V and VI indicate that alkalized activated carbons (prior art catalysts) give low TBF removal over a range of temperatures for 220°–353° F. The alkalized activated carbon catalysts are much less effective than the catalysts of the instant invention in the destruction of organic formates and free acids.

TABLE V

Summary for TBA Dehydration and Contaminants Decomposition Over Alkalized, Activated Carbon
Catalyst ID: Alkalized, Activated Carbon

| Bed Temperature °F. | TBA Conversion (Wt. %) | TBF Removal (Wt %) | DTBP Removal (Wt %) | Weight Percent Recovery (%) | SAP No. pH = 11 | SAP No. pH = 7 |
|---|---|---|---|---|---|---|
| 179 | 1.1 | 17.7 | 1.6 | 98.8 | | |
| 220 | 5.5 | 23.6 | 9.3 | 95.1 | 7.87 | 5.84 |
| 268 | 2.4 | 22.7 | 35.4 | 97.3 | 8.24 | 5.83 |
| 284 | 39.2 | 52.8 | 68.0 | 69.7 | 8.76 | 6.23 |
| 309 | 53.9 | 51.5 | 94.5 | 91.3 | 8.02 | 6.13 |
| 327 | 19.2 | 40.7 | 98.2 | 84.5 | 8.42 | 5.88 |

TABLE VI

Summary for TBA Dehydration and Contaminants Decomposition Over Alkalized, Activated Carbon
Catalyst ID: 052-95-2616-0000, Alkalized, Activated Carbon

| Bed Temperature °F. | TBA Conversion (Wt. %) | TBF Removal (Wt %) | DTBP Removal (Wt %) | Weight Percent Recovery (%) | SAP No. pH = 11 | SAP No. pH = 7 |
|---|---|---|---|---|---|---|
| 188 | 17.9 | 18.2 | 2.5 | 108.5 | | |
| 234 | 46.9 | 61.7 | 54.0 | 64.1 | 6.31 | 5.43 |
| 282 | 12.3 | 43.7 | 54.9 | 89.8 | 5.51 | 4.57 |
| 308 | 8.7 | 46.5 | 84.6 | 92.3 | 5.16 | 4.37 |
| 328 | 6.7 | 53.5 | 100.0 | 93.7 | 5.18 | 4.32 |
| 353 | 7.6 | 72.8 | 100.0 | 93.2 | 4.49 | 3.97 |

In summary, this invention provides a process for purification of TBA and MTBE streams. The formate esters (TBF and MeF) and formic acid as well as peroxides (DTBP and ATBP) can be removed by contacting the TBA feed with a DHT-4A/Alumina based catalyst containing Group IB and VIII metals. The reactor suitable for this process may be fixed-bed, ebullated-bed and catalytic distillation reactor. The desired process temperature and pressure are 250°–500° F. and 100–600 psi. The total metal content may be in the range of 0–40 wt % of the final catalyst. The concentration of DHT-4A in the support may range from 5–100%.

We claim:

1. A process for decomposing impurities consisting essentially of formate esters, free acids and peroxides in a tertiary butyl alcohol stream to produce noncondensible gas products which comprises reacting said tertiary butyl alcohol stream or a methyl tertiary butyl ether stream containing said impurities over a catalyst consisting essentially of a non-noble Group VIII metal and a metal of Group IB on an inert support consisting essentially of alumina mixed with a hydrotalcite-like composition in the proportions of 2–75 wt. % alumina and 25–98 wt. % of hydrotalcite-like composition.

2. The process of claim 1 wherein the noncondensible gas products are hydrogen, carbon monoxide, carbon dioxide and methane.

3. The process of claim 1 wherein the catalyst contains 0.1–6 wt % non-noble Group VIII, and 1–30 wt % Group IB as oxides.

4. The process of claim 1 wherein said hydrotalcite-like composition has the formula:

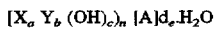

wherein a=1–10 b=1–10 c=2; (a+b)=4–40

A is an anion of formal negative charge n n=an integer 1–4 d is the formal positive charge of $[X_a Y_b (OH)_c]$ e=1–10

X— is a divalent metal

Y is a trivalent metal of Group III or Group VI-B or non-noble Group VIII of the Periodic Table subject to the qualification that when one of d or n is an integral multiple of the other, they are both reduced to lowest integral terms.

5. The process of claim 4 wherein X is magnesium.

6. The process of claim 4 wherein a is 3–6.

7. The process of claim 4, wherein b is 1–3.

8. The process of claim 4, wherein c is 10–16.

9. The process of claim 4 wherein said hydrotalcite-like composition is hydrotalcite, represented by the formula:

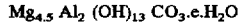

wherein e is 1–4.

10. The method of claim 6 wherein said hydrotalcite-like composition is

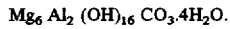

11. The method of claim 4 wherein said hydrotalcite-like composition is

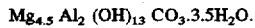

12. The process of claim 11 wherein said Group IB is present in an amount of 1 wt. % to 30 wt. %.

13. The process of claim 1 wherein said Group IB metal is copper.

14. The process of claim 1 wherein said Group VIII metal is present in an amount from 0.1 wt. % to 6 wt. %.

15. The process of claim 1 wherein said Group VIII metal is nickel.

16. A process for decomposing formate esters in a tertiary butyl alcohol stream or a methyl tertiary butyl [alcohol] ether stream to produce noncondensible gas products which comprises reacting said tertiary butyl alcohol or methyl tertiary butyl ether stream containing formate esters at a temperature of 250°–500° F., a pressure of 100°–600 psi, and a liquid hourly space velocity (LHSV) of 0.1–10/hr over a catalyst [comprising] consisting essentially of 6–12 wt. % copper and 0.5–1 wt. % nickel on a support [comprising] consisting essentially of 75 wt. % to 25 wt. % of alumina and 25 wt. % to 75 wt. % of a hydrotalcite-like composition having the formula:

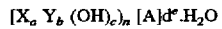

wherein a=1–10 b=1–10 c=2 (a+b)=4–40

A is an anion of formal negative charge n=an integer of 1–4 d is the formal positive charge of $[X_a Y_b (OH)_c]$ e=1–10

X is a divalent metal, and

Y is a trivalent metal of Group III or Group VIB or non-noble Group VIII of the Periodic Table subject to the qualification that when one of d or n is an integral multiple of the other, they are both reduced to the lowest integral terms.

* * * * *